(12) United States Patent
Takeuchi et al.

(10) Patent No.: US 8,877,130 B2
(45) Date of Patent: Nov. 4, 2014

(54) DEVICE FOR MEASURING BIOLOGICAL SAMPLE

(75) Inventors: Yoshiki Takeuchi, Ehime (JP); Toshiki Matsumoto, Ehime (JP); Eiji Okuda, Ehime (JP); Kiyohiro Horikawa, Ehime (JP); Takahiro Watanabe, Ehime (JP); Kaoru Shigematsu, Ehime (JP); Yoshinori Amano, Ehime (JP); Shinichi Kojima, Ehime (JP)

(73) Assignee: Panasonic Healthcare Co., Ltd., Ehime (JP)

( * ) Notice: Subject to any disclaimer, the term of this patent is extended or adjusted under 35 U.S.C. 154(b) by 2 days.

(21) Appl. No.: 13/807,388

(22) PCT Filed: Sep. 7, 2011

(86) PCT No.: PCT/JP2011/005020
§ 371 (c)(1),
(2), (4) Date: Dec. 28, 2012

(87) PCT Pub. No.: WO2012/042757
PCT Pub. Date: Apr. 5, 2012

(65) Prior Publication Data
US 2013/0108510 A1    May 2, 2013

(30) Foreign Application Priority Data
Sep. 29, 2010   (JP) ................................ 2010-218184
Dec. 28, 2010   (JP) ................................ 2010-291925

(51) Int. Cl.
*G01N 33/00*   (2006.01)
*G01N 33/50*   (2006.01)
*G01N 27/327*   (2006.01)

(52) U.S. Cl.
CPC ............ *G01N 33/50* (2013.01); *G01N 27/3273* (2013.01)
USPC ...................... 422/82.12; 422/400; 422/82.01

(58) Field of Classification Search
CPC ...................................................... G01N 33/521
USPC ........................ 204/403.04; 422/82.01, 82.12
See application file for complete search history.

(56) References Cited

U.S. PATENT DOCUMENTS 8,164,468 B2    4/2012   Gofman et al.
8,354,013 B2 *  1/2013   Bommakanti et al. ... 204/403.04
(Continued)

FOREIGN PATENT DOCUMENTS

JP    2007-010317    1/2007
JP    2007-526440    9/2007
(Continued)

OTHER PUBLICATIONS

International Search Report issued Oct. 25, 2011 in International (PCT) Application No. PCT/JP2011/005020.

*Primary Examiner* — Sam P Siefke
(74) *Attorney, Agent, or Firm* — Wenderoth, Lind & Ponack, LLP (57) ABSTRACT

A partition wall is provided between a display section and a sensor mount inside a main case. A control board housing chamber is disposed on the display unit side of the partition wall, and a measurement board housing chamber is disposed on the sensor mount side of the partition wall. A control board is housed in the control board housing chamber, and a measurement board and a temperature sensor are housed in the measurement board housing chamber.

15 Claims, 7 Drawing Sheets

(56) References Cited

U.S. PATENT DOCUMENTS

2006/0229502 A1 10/2006 Pollock et al.
2007/0025877 A1 2/2007 Hansen
2009/0146826 A1 6/2009 Gofman et al.
2010/0268475 A1 10/2010 Kusumoto
2012/0181991 A1 7/2012 Gofman et al.

FOREIGN PATENT DOCUMENTS

| | | |
|---|---|---|
| WO | 2009/075696 | 6/2009 |
| WO | 2009/119116 | 10/2009 |

* cited by examiner

DEVICE FOR MEASURING BIOLOGICAL SAMPLE

TECHNICAL FIELD

The present invention relates to a biological sample measuring device which measures blood glucose levels, for example.

BACKGROUND ART

A conventional biological sample measuring device has the following configuration.

Specifically, a conventional biological sample measuring device comprised a main case, a display section and sensor mount disposed at locations away from the outer surface of this main case, a control board provided inside the main case and connected to this display section, a measurement board provided inside the main case and connected to the sensor mount, and a temperature sensor disposed on or near this measurement board (see the following Patent Literature 1, for example).

CITATION LIST

Patent Literature

Patent Literature 1: Japanese Unexamined Patent Application Publication (Translation of PCT Application) No. 2007-526440

SUMMARY

However, the following problems were encountered with the above-mentioned conventional bio logical sample measuring device.

Specifically, with the conventional configuration discussed above, blood was deposited on a biosensor mounted to the sensor mount, the blood glucose level was measured by the measurement board, and the blood glucose level thus measured was displayed on the display section via the control board.

The temperature sensor here is provided in order to correct the temperature dependence characteristics of the biosensor by measuring the temperature near the measurement board. Specifically, the higher the temperature is in the ambient environment, the more the reaction proceeds and the larger the measurement value outputted by the biosensor. Therefore, the temperature at this point is detected by the temperature sensor and used to correct to the proper measurement value.

Technical Problem

A problem with the conventional configuration discussed above was that the measurement accuracy ended up being low.

Specifically, the temperature sensor measures the ambient environment temperature of the biosensor, but near this temperature sensor there is a control board that is in a perpetual state of elevated temperature due to controlling the display section, etc. Therefore, the temperature detected by the temperature sensor ends up being higher than the actual ambient environment temperature of the biosensor. As a result, there is the risk that the temperature near this control board may adversely affect the temperature sensor.

Because of the above, there is the risk that the measurement value corrected using this somewhat higher detected temperature will end up being lower (for example) than the normal state, that is, that the measurement accuracy will end up being low.

In view of this, it is an object of the present invention to raise the measurement accuracy of the ambient environment temperature detected by a temperature sensor.

Solution to Problem

To achieve the stated object, the present invention comprises a main case, a display section, a sensor mount, a control board, a measurement board, a temperature sensor, a partition wall, a control board housing chamber, and a measurement board housing chamber. The display section and the sensor mount are disposed at locations away from each other on the outer surface of the ms. The control board is connected to the display section and is provided inside the main case. The measurement board is connected to the sensor mount and is provided inside the main case. The temperature sensor is disposed on or near the measurement board. The partition wall is provided between the display section and the sensor mount inside the main case. The control board housing chamber is disposed on the display section side of the partition wall and houses the control board. The measurement board housing chamber is disposed on the sensor mount side of the partition wall and houses the measurement board and the temperature sensor.

Advantageous Effects

With the present invention, since the partition wall is provided between the display section and the sensor mount inside the main case, the control board housing chamber is disposed on the display section side of the partition wall, the measurement board housing chamber is disposed on the sensor mount side of the partition wall, the control board is housed in this control board lousing chamber, and the measurement board is housed in the measurement board housing chamber, heat from the control board housing chamber is blocked by the partition wall and can be prevented from being transmitted to the measurement board housing chamber. As a result, the temperature sensor of the measurement board provided in this measurement board housing chamber can detect the temperature close to the ambient environment of the biosensor, and the measurement value of the biosensor can be properly corrected, so measurement accuracy can be improved.

DESCRIPTION OF EMBODIMENTS

The biological sample measuring device (device for measuring a biological sample) pertaining to an embodiment of the present invention will be described through reference to the appended drawings.

A biological sample measuring device for measuring blood glucose level will be described in this embodiment.

Figure 1:
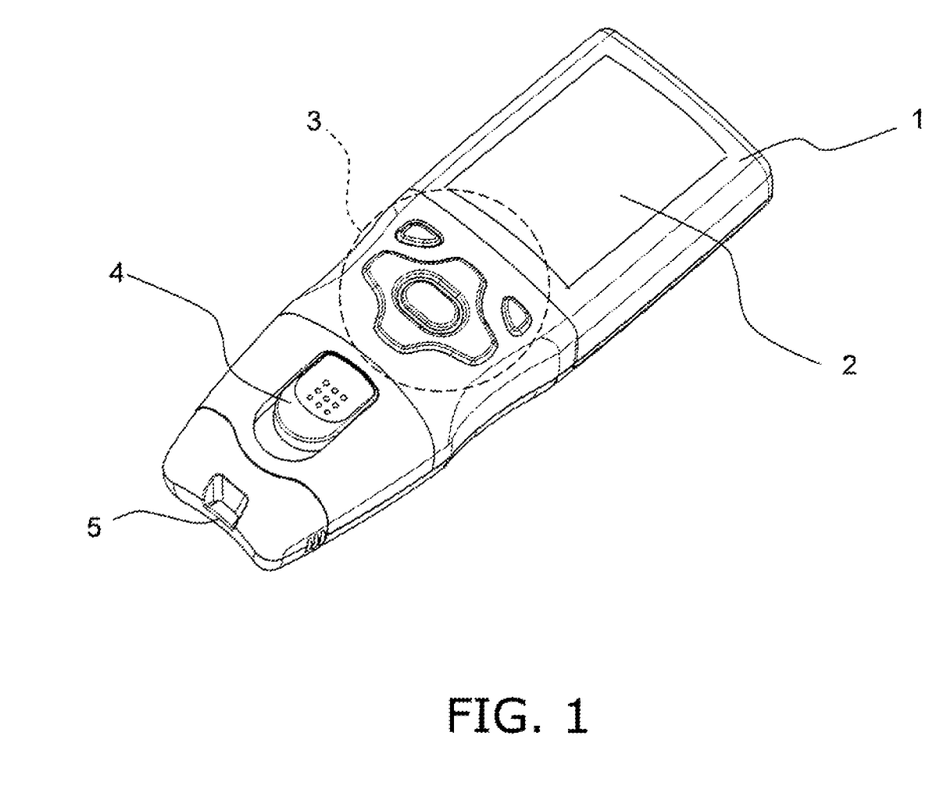
FIG. 1 is an oblique view of the configuration of the biological sample measuring device pertaining to an embodiment of the present invention.

As shown in FIG. 1, the biological sample measuring device in this embodiment comprises a substantially cuboid main case 1, a display section 2, a user interface 3, a sensor eject lever 4, and a sensor mount 5.

As shown in FIG. 1, the display section 2 is disposed on a first end side of the outer surface of the main case 1, the user interface 3 and the sensor eject lever 4 are disposed in the middle portion, and the sensor mount 5 is disposed on a second end side that is on the opposite side limn the first end. That is, the display section 2 and the sensor mount 5 are disposed away from each other on the outer surface of the main case 1, on opposite sides in the lengthwise direction of the biological sample measuring device.

Figure 2:
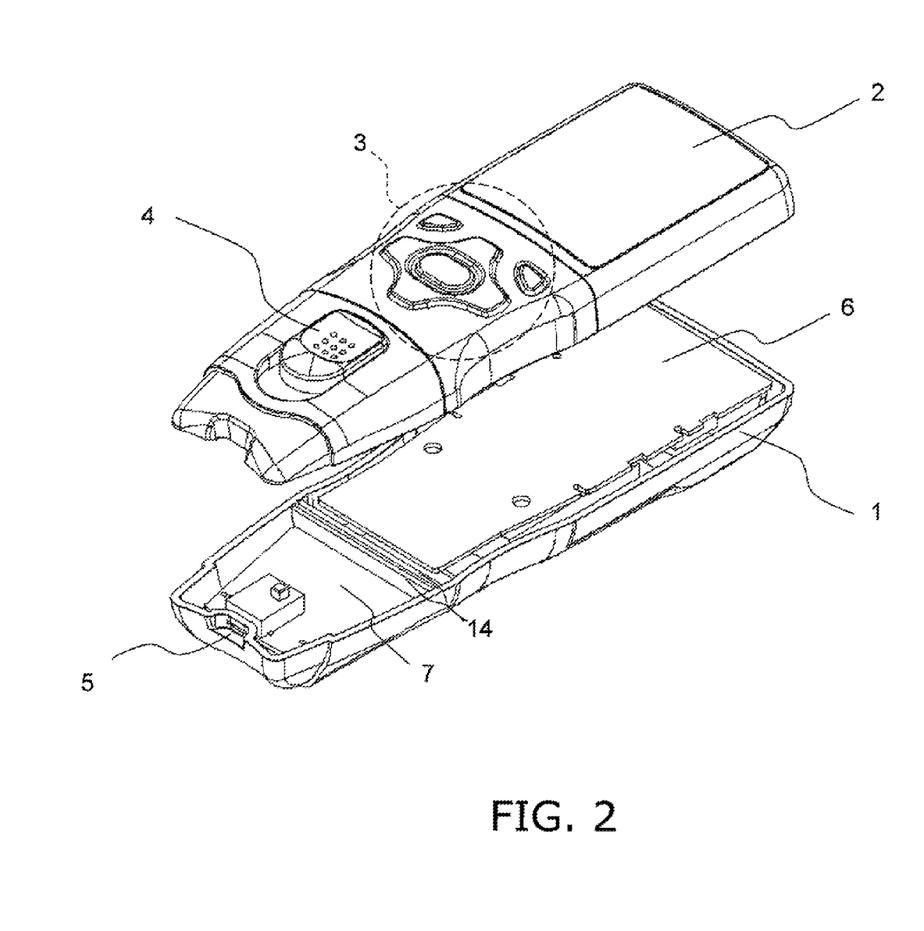
FIG. 2 is an exploded oblique view of the biological sample measuring device in FIG. 1.
Figure 3:
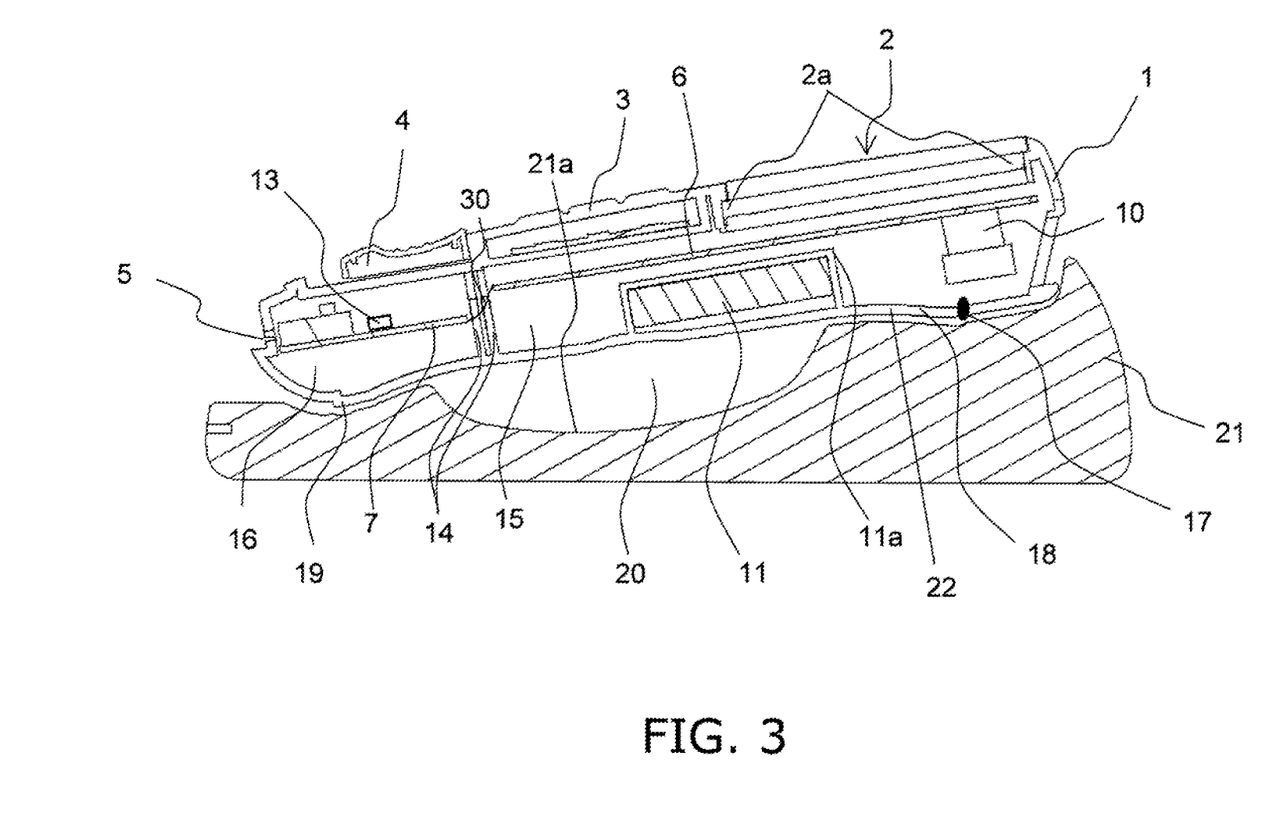
FIG. 3 is a cross section of the biological sample measuring device in FIG. 1.

As shown in FIGS. 2 and 3, a control board 6 is housed in a portion corresponding to the display section 2 and the user interface 3 inside the main case 1. A measurement board 7 is housed in a portion corresponding to the sensor eject lever 4 and the sensor mount 5 inside the main case 1.

Figure 4:
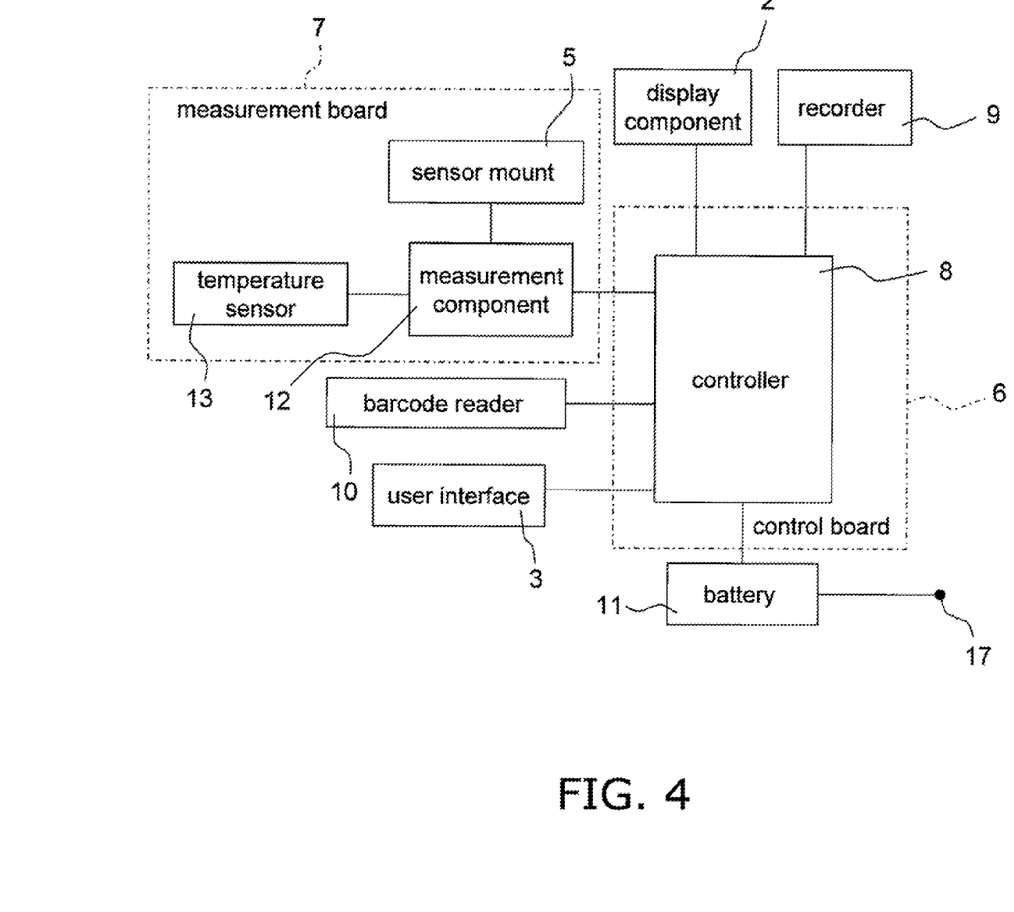
FIG. 4 is an electrical block diagram of the biological sample measuring device in FIG. 1.

The main component of the control board 6 is the controller 8 shown in FIG. 4. The controller 8 is connected to the display section 2, the user interface 3, a recorder 9, a barcode reader 10, and a rechargeable battery 11. The control board 6 and the measurement board 7 are connected with a flexible cable 30 (see FIG. 3, etc.).

Meanwhile, the measurement board 7 connects a temperature sensor 13 and a measurement section 12 provided on this board. The measurement section 12 and the controller 8 are electrically connected. As shown in FIG. 3, the measurement board 7 is provided as a separate board from the control board 6, and is connected to the control board 6 via the flexible cable 30.

With the biological sample measuring device in this embodiment, a biosensor (not shown) is inserted into the sensor mount 5 shown in FIG. 1, and blood is deposited on the biosensor in this mounted state, whereupon the blood glucose level is measured by the measurement section 12.

The ambient temperature near the sensor mount 5 at this point is detected by the temperature sensor 13. In this embodiment, the blood glucose level is corrected on the basis of the temperature detected by the temperature sensor 13. The corrected blood glucose level is displayed on the display section 2 via the controller 8.

As shown in FIGS. 2 and 3, with the biological sample measuring device in this embodiment, a partition wall 14 is provided between the display section 2 and the sensor mount 5 inside the main case 1. A control board housing chamber 15 is disposed on the display section 2 side of the partition wall 14, and a measurement board housing chamber 16 is disposed on the sensor mount 5 side of the partition wall 14. Furthermore, in this embodiment, the control board 6 is housed in the control board housing chamber 15, and the measurement board 7 and the temperature sensor 13 are housed in the measurement board housing chamber 16.

Specifically, since the controller 8 is mounted on the control board 6, its operation raises the temperature. Also, the display section 2 raises the temperature at its backlight 2a portion. Furthermore, the barcode reader 10 raises the temperature from its reading light source. Also, the battery 11 raises the temperature at its battery module 11a portion during charging.

Accordingly the control board housing chamber 15 that houses or is near these components undergoes a considerable temperature elevation during actual use. It is undesirable for this temperature elevation to have an adverse effect on the temperature sensor 13 of the measurement board 7.

With the biological sample measuring device in this embodiment, as mentioned above, the partition wall 14 is provided between the display section 2 and the sensor mount 5 inside the main case 1. Also, the control board housing chamber 15 is disposed on the display section 2 side of the partition wall 14, and the measurement board housing chamber 16 is disposed on the sensor mount 5 side of the partition wall 14. Further, the control board housing chamber 15 houses the control board 6, and the measurement board housing chamber 16 houses the measurement board 7 and the temperature sensor 13.

Consequently, the constituent elements that are a source of heat, such as the light source of the barcode reader 10, the backlight 2a, and the control board 6 built into the biological sample measuring device, are gathered together within the control board housing chamber 15, and can be isolated by the partition wall 14 from the measurement board housing chamber 16 in which the temperature sensor 13 is housed. Thus, the temperature of the control board housing chamber 15 has less adverse effect on the temperature sensor 13 of the measurement board housing chamber 16. As a result, the blood glucose level measured by the measurement section 12 can be properly corrected on the basis of the actual ambient temperature near the sensor mount 5 detected by the temperature sensor 13. Therefore, the accuracy at which the blood glucose level is measured by the measurement section 12 can be improved over that in the past.

Also, with this embodiment, as shown in FIGS. 2 and 3, a plurality (two) of the partition walls 14 are disposed at a specific spacing.

Consequently, the space between the partition walls 14 functions as a thermally insulating space, so the above-mentioned movement of heat from the control board housing chamber 15 to the measurement board housing chamber 16 can be effectively prevented.

Also, with the biological sample measuring device in this embodiment, the control board 6 and the measurement board 7 are connected to each other via the flexible cable 30. Also, the partition walls 14 provided for the above-mentioned heat blocking are provided so as to sandwich the flexible cable 30 from above and below.

Consequently, even though the control board 6 and the measurement board 7 are provided as separate boards, if the partition walls 14 are provided at a location in the main case 1 corresponding to the thick flexible cable 30, electrical connection can be ensured between the control board 6 and the measurement board 7, and the space between the control board housing chamber 15 and the measurement board housing chamber 16 can be blocked off with as little gap as possible.

Next, other features of this embodiment will be described.

As shown in FIG. 3, in this embodiment the battery 11 is disposed below the control board 6 inside the control board housing chamber 15 of the main case 1. A charging terminal 17 for the battery 11 is disposed on the opposite side from the sensor mount 5, on the rear face side of the main case 1. A protrusion 18 (first protrusion) that protrudes below the portion of the main case 1 in which the battery 11 is disposed in a state in which the device has been placed in a cradle 21 is formed on the rear face portion of the main case 1 where the charging terminal 17 is disposed.

Also, a protrusion 19 (second protrusion) that protrudes below the portion of the main case 1 in which the battery 11 is disposed is formed at the portion where the measurement board 7 is disposed on the rear face portion of the main case 1.

In other words, with the biological sample measuring device of this embodiment, the protrusions 18 and 19, which protrude toward the cradle 21, are formed ahead of and behind the portion where the battery 11 is housed, on the rear face side of the main case 1.

Figure 6:
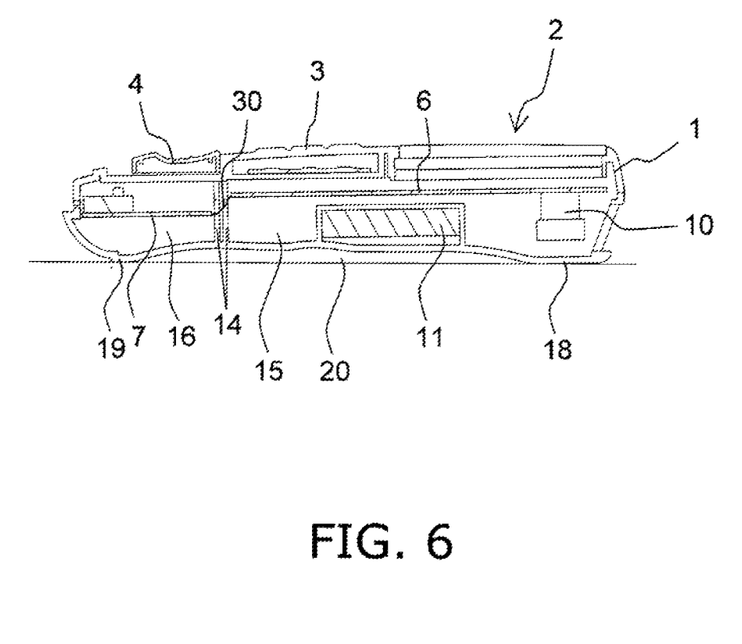
FIG. 6 is a lateral cross section of the state when the biological sample measuring device in FIG. 1 has been placed on a level surface.

Consequently, as shown in FIG. 6, in a state in which the biological sample measuring device has been placed on a table or other level surface, a space 20 is formed underneath the battery 11 on the rear face side of the main case 1.

Also, in this embodiment, a recess 21a is formed in the portion of the cradle 21 that is opposite and below the battery 11 on the rear face side of the main case 1, so that this space 20 can be even larger.

More specifically, as shown in FIG. 3, when the battery 11 is being charged through the charging terminal 17 in a state in which the main case 1 has been put in the cradle 21, the temperature inside the control board housing, chamber 15 can rise quite high due to prolonged charging.

In view of this, in this embodiment, as discussed above, the protrusions 18 and 19 are provided ahead of and behind the portion where the battery 11 is housed, on the rear face side of the main case 1. Furthermore, the recess 21a is provided to the portion of the cradle 21 that is opposite the part housing the battery 11 on the rear face side of main case 1.

Consequently, the space 20 formed under the battery 11 functions as a heat dispersal space. Thus, during charging, heat generated at the battery portion is released into this space 20 suppresses the rise in temperature inside the control board housing chamber 15.

As a result, even when blood glucose level is measured by the sensor mount 5 immediately after the charging of the battery 11, the increase in the temperature near the sensor mount 5 can be kept to a level that will substantially not affect the measurement. Thus, even in such situations when the temperature inside the control board housing chamber 15 is prone to rising, the adverse effect that this temperature elevation has on the temperature sensor 13 can be kept to a minimum, and measurement accuracy can be improved over that in the past.

Furthermore, in this embodiment measurement accuracy can be improved by separating the control board 6 and the measurement board 7 so that they are provided as independent boards.

Specifically, with a conventional configuration, the control board and the measurement board were formed integrally as a single, large board (not shown). Therefore, if the temperature rose because of operation of the controller, then in the case of a multilayer board, for example, there was the risk that heat would move through the large copper foil pattern (not shown) used for power supply within the board, and reach the measurement section or the temperature sensor.

In contrast, with the biological sample measuring device in this embodiment, the control board 6 and the measurement board 7 are separated and provided as independent boards. The control board 6 is housed in the control board housing chamber 15, and the measurement board 7 is housed in the measurement board housing chamber 16.

Therefore, even if operation of the controller 8 raises the temperature and this heat is transferred to the control board 6, since the control board 6 and the measurement board 7 are physically separated, the heat of the control board 6 can be prevented from being directly transferred to the temperature sensor 13 provided on the measurement board 7. That is, in this respect as well, the temperature inside the control board housing chamber 15 will not have as much elect on the temperature sensor 13 of the measurement board housing chamber 16, and as a result measurement accuracy can be improved.

In this embodiment, the control board 6 and the measurement board 7 are connected to each other via the flexible cable 30 as mentioned above. This flexible cable 30 has a power wire (not shown) from the battery 11 to the measurement board 7, and a signal wire (not shown) that transmits digital measurement data of the measurement section 12. Since the measurement section 12 consumes little power, these power lines can be very fine. Therefore, the flexible cable 30 will not transfer a large amount of heat.

Furthermore, in this embodiment, as mentioned above, the measurement board 7 is housed in the measurement board housing chamber 16 along with the temperature sensor 13. Therefore, measurement accuracy by the biological sample measuring device can be enhanced.

Specifically, a temperature acquisition section (not shown) connected to the temperature sensor 13, and a blood glucose level measurement circuit (not shown) connected to a biosensor (not shown) are provided inside the measurement section 12 of the measurement board 7. The temperature acquisition section and blood glucose level measurement circuit are constituted by an analog circuit (analog/digital converter) having temperature characteristics. Therefore, when the temperature elevation of the control board housing chamber 15 is transferred to the analog circuit of the measurement section 12, there is the risk that this will adversely affect the blood glucose level measurement accuracy.

In contrast, with the biological sample measuring device of the present invention, the measurement board 7 is housed in the measurement board housing chamber 16 along with the temperature sensor 13. Also, as mentioned above, the temperature inside the control board housing chamber 15 has little effect on the temperature sensor 13 of the measurement board housing, chamber 16, so the temperature acquisition section (not shown) and the blood glucose level measurement circuit (not shown) provided inside the measurement section 12 of the measurement board 7 can operate stably, being affected very little by temperature. As a result, the measurement accuracy of the biological sample measuring device can be improved.

Also, because the control board 6 and the measurement board 7 are separated as independent boards, the stiffness of the individual boards can be increased over that of a configuration in which the control board and the measurement board are disposed on a conventional single, large board. Accordingly, resistance to the impact of falling, etc., can be increased while the movement of heat from the control board housing chamber 15 to the measurement board housing chamber 16 can be effectively prevented.

Also, as shown in FIG. 3, with the biological sample measuring device pertaining to this embodiment, an inclined face produced by inclining the face of the protrusion 18 on the sensor mount 5 side toward the surface side of the main case is formed on the protrusion 18 provided on the control board housing chamber 15 side of the rear face of the main case 1. A concave finger rest 22 that conforms to the shape of the fingers is also provided to the surface portion of this inclined face.

Specifically, when the blood glucose level of a patient is measurement in a hospital, a nurse, for example, performs the measurement by grasping the outer periphery of the main case 1. If there are numerous patients, the measurement needs to be carried out continuously. In a case such as this, there is the risk that the heat of the nurse's palm holding the main case 1 will be transferred into the interior of the main case 1 and significantly raise the temperature.

In view of this, in this embodiment, as discussed above, the concave finger rest 22 is provided to the protrusion 18. That is, the concave finger rest 22 is provided to the outer surface of the control board housing chamber 15 the outer periphery of the main case 1).

Accordingly, the part of the main case 1 that is to be grasped will be clear to the user.

Figure 5:
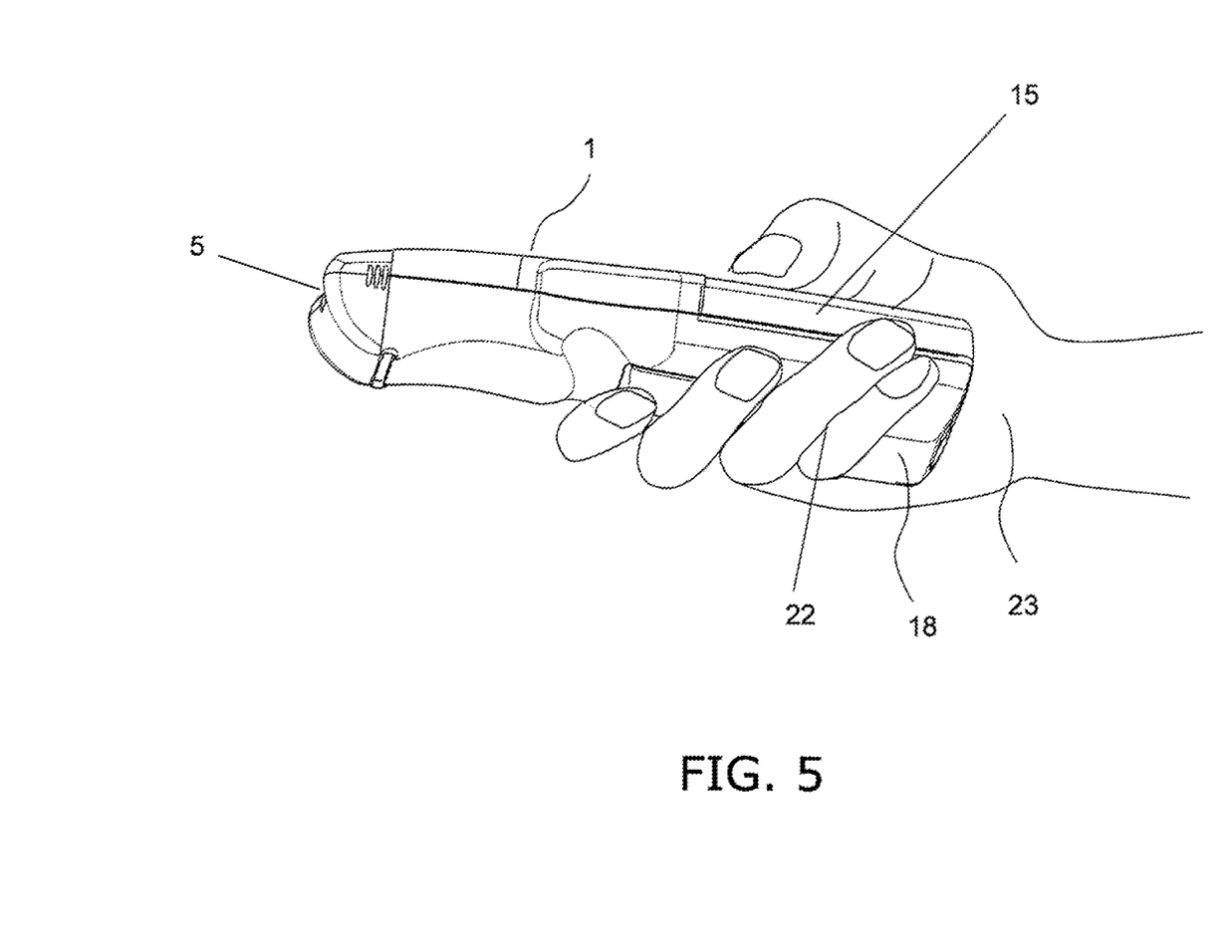
FIG. 5 is an oblique view of the usage state of the biological sample measuring device in FIG. 1.

Therefore, as shown in FIG. 5, the user the user places the little finger and the ring finger of the right hand 23 on this finger rest 22, grasps the outer surface of the control board housing chamber 15 (the outer periphery of the main case 1) with the palm, and operates the device in this state.

Therefore, heat from the palm will transfer through the main case 1 to the control board housing chamber 15, but heat from the hand is not as likely to transfer to the measurement board housing chamber 16 that is not held in the fingers. Also, since the movement of heat from the control board housing chamber 15 to the measurement board housing chamber 16 is effectively prevented by the partition walls 14, heat can be prevented from being transferred to the measurement board housing chamber 16 in this respect as well.

As a result, heat transferred from the palm to the control board housing chamber 15 will have less effect on the temperature sensor 13 of the measurement board housing chamber 16, so the measurement accuracy of the biological sample measuring device can be improved.

Other Embodiments

An embodiment of the present invention was described above, but the present invention is not limited to or by the above embodiment, and various modifications are possible without departing from the gist of the invention.

(A)

In the above embodiment, an example was described in which the protrusions 18 and 19 were provided to the portions ahead of and behind (in the lengthwise direction) the portion where the battery 11 is housed, and the recess 21*a* was also provided on the cradle 21 side, in order to effectively disperse the heat produced around the portion where the battery 11 is housed inside the main case 1. However, the present invention is not limited to this.

For example, a recess does not necessarily have to be formed on the cradle 21 side, and a heat dispersal space (space 20) may be formed under the battery housing portion by the protrusions 18 and 19 on the main case 1 side.

Here again, as shown in FIG. 6, the space 20 can be formed under the portion where the battery 11 is housed on the rear face side of the main case 1.

(B)

In the above embodiment, an example was described in which two partition walls 14 were provided to separate the control board housing chamber 15 from the measurement board housing chamber 16, but the preen invention is not limited to this.

For example, there may be only one partition wall that separates the control board housing chamber from the measurement board housing chamber, or there may be three or more.

(C)

In the above embodiment, an example was described in which the control board 6 and the measurement board 7 provided as independent boards inside the main case 1 were connected to each other via the flexible cable 30, but the present invention is not limited to this.

For example, the control board 6 and the measurement board 7 provided as independent boards inside the main case 1 may be connected wirelessly. Alternatively, the control board and the measurement board may be provided on a single board, and the space between them blocked by a partition wall.

(D)

In the above embodiment, an example was described in which the partition walls 14 were provided so as to minimize the gap between the control board housing chamber and the measurement board housing chamber, at the portion of the main case 1 corresponding to the flexible cable 30 that connected the control board 6 and the measurement board 7, but the present invention is not limited to this.

Figure 7:
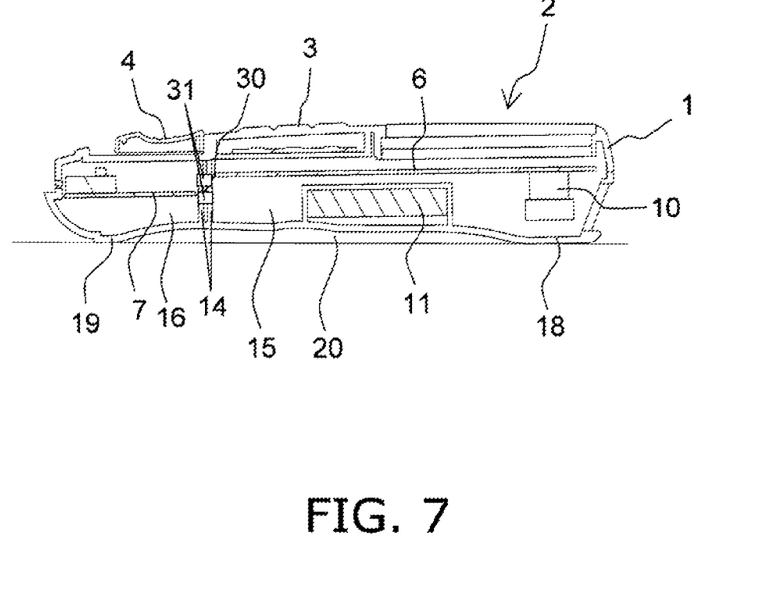
FIG. 7 is a lateral cross section of the configuration of the biological sample measuring device pertaining to another embodiment of the present invention.

For example, as shown in FIG. 7, a cushioning member 31 may be provided to the portion of the partition walls 14 opposite the flexible cable 30, and the space between the control board housing chamber and the measurement board housing chamber completely blocked off.

In this case, even though the cushioning member 31 touches the flexible cable 30, it will not damage the flexible cable 30, and the movement of heat between the control board housing chamber and the measurement board housing chamber can be effectively blocked.

INDUSTRIAL APPLICABILITY

As discussed above, with the present invention, the measurement value produced by a biosensor can be properly corrected, and the measurement accuracy of blood glucose level or the like can be improved, by raising the measurement accuracy of the ambient environment temperature of a temperature sensor, so the present invention is expected to find wide application as a device for measuring biological information such as blood glucose levels.

REFERENCE SIGNS LIST

1 main case
2 display section
2*a* backlight
3 user interface
4 sensor eject lever
5 sensor mount
6 control board
7 measurement board
8 controller
9 recorder
10 barcode reader
11 battery
12 measurement section
13 temperature sensor
14 partition wall
15 control board housing chamber
16 measurement board housing chamber
17 charging terminal.
18 protrusion (first protrusion)
19 protrusion (second protrusion)
20 space
21 cradle
21*a* recess (concave space)
30 flexible cable
31 cushioning member

The invention claimed is:
1. A device for measuring a biological sample, comprising:
a main case;
a display section and a sensor mount that are disposed away from each other on the outer surface of the main case;

a control board that is connected to the display section and is provided inside the main case;
a measurement board that is connected to the sensor mount and is provided inside the main case;
a temperature sensor that is disposed on or near the measurement board;
a partition wall that is provided between the display section and the sensor mount inside the main case;
a control board housing chamber that is disposed on the display section side of the partition wall and houses the control board; and
a measurement board housing chamber that is disposed on the sensor mount side of the partition wall and houses the measurement board and the temperature sensor.

2. The device for measuring a biological sample according to claim 1, wherein the partition wall is a first partition wall, and the device further comprises a second partition wall spaced apart from the first partition wall.

3. The device for measuring a biological sample according to claim 1, further comprising:
a battery housing space that is disposed under the control board inside the control board housing chamber;
a battery charging terminal that is disposed on the rear face side of the main case, on the opposite side from the sensor mount side, and is housed in the battery housing space;
a first protrusion that is formed so as to protrude below the main case portion in which the battery is disposed, in the rear face-side portion of the main case in which the charging terminal is disposed; and
a second protrusion that is formed so as to protrude below the main case portion in which the battery is disposed, in the portion in which the measurement board is disposed on the rear face side of the main case.

4. The device for measuring a biological sample according to claim 3, wherein the first protrusion has an inclined face produced by inclining a face of the first protrusion on the sensor mount side toward the surface side of the main case, and
further comprising a finger rest that is provided to the inclined face.

5. The device for measuring a biological sample according to claim 4, wherein the finger rest is provided to the outer surface portion of the control board housing chamber of the main case.

6. The device for measuring a biological sample according to claim 1, wherein the control board and the measurement board are provided as separate boards.

7. The device for measuring a biological sample according to claim 6, wherein the control board and the measurement board are connected to each other via a flexible cable.

8. A device for measuring a biological sample, the device comprising:
a main case;
a display section and a sensor mount that are disposed away from each other on the outer surface of the main case;
a control board that is connected to the display section and is provided inside the main case;
a measurement board that is connected to the sensor mount and is provided inside the main case;
a temperature sensor that is disposed on or near the measurement board;
a partition wall that is provided between the display section and the sensor mount inside the main case;
a control board housing chamber that is disposed on the display section side of the partition wall and houses the control board;
a measurement board housing chamber that is disposed on the sensor mount side of the partition wall and houses the measurement board and the temperature sensor; and
a cushioning member that is provided to the portion inside the main case that comes into contact with the flexible cable, and that blocks the space between the control board housing chamber and the measurement board housing chamber formed inside the main case,
wherein the control board and the measurement board are provided as separate boards, and
wherein the control board and the measurement board are connected to each other via a flexible cable.

9. The device for measuring a biological sample according to claim 1, further comprising:
a cradle in which the main case is placed and which charges the battery housed in the main case; and
a concave space formed in part of the cradle opposite the battery housing space disposed below the control board.

10. The device for measuring a biological sample according to claim 1, wherein the sensor mount is configured to have a sensor inserted therein for taking a measurement, and
wherein the control board includes a controller configured to correct the measurement based on a temperature detected by the temperature sensor.

11. The device for measuring a biological sample according to claim 1, wherein the partition wall is configured to isolate the measurement board housing chamber from the control board housing chamber such that a temperature of the control board housing chamber has less effect on the temperature sensor disposed in the measurement board housing chamber.

12. A device for measuring a biological sample, the device comprising:
a main case including a control board housing chamber and a measurement board housing chamber, the control board housing chamber and the measurement board housing chamber being provided inside the main case;
a display section and a sensor mount that are disposed away from each other on an outer surface of the main case;
a control board housed in the control board housing chamber, the control board being connected to the display section;
a measurement board housed in the measurement board housing chamber, the measurement board being connected to the sensor mount;
a temperature sensor disposed in the measurement board housing chamber, the temperature sensor being disposed on or near the measurement board; and
a partition wall provided between the control board housing chamber and the measurement board housing chamber, the partition wall being configured to physically isolate the measurement board housing chamber from the control board housing chamber.

13. The device for measuring a biological sample according to claim 12, wherein the partition wall is configured to isolate the measurement board housing chamber from the control board housing chamber such that a temperature of the control board housing chamber has less effect on the temperature sensor disposed in the measurement board housing chamber.

14. The device for measuring a biological sample according to claim 13, wherein the sensor mount is configured to have a sensor inserted therein for taking a measurement, and
wherein the control board includes a controller configured to correct the measurement based on a temperature detected by the temperature sensor.

15. The device for measuring a biological sample according to claim 12, wherein the sensor mount is configured to have a sensor inserted therein for taking a measurement, and wherein the control board includes a controller configured to correct the measurement based on a temperature detected by the temperature sensor.

\* \* \* \* \*